United States Patent [19]

Weisenborn et al.

[11] 4,104,400
[45] Aug. 1, 1978

[54] IMIDAZO(2,1-b)THIAZOLE DERIVATIVES, COMPOSITIONS CONTAINING SAME, AND METHOD OF TREATING HELMINTHIASIS

[75] Inventors: Frank Lee Weisenborn; Rudiger D. Haugwitz, both of Titusville; Frederic Peter Hauck, Somerville, all of N.J.

[73] Assignee: E. R. Squibb & Sons, Inc., Princeton, N.J.

[21] Appl. No.: 813,910

[22] Filed: Jul. 8, 1977

[51] Int. Cl.² ............... C07D 513/04; A61K 31/425
[52] U.S. Cl. ............... 424/270; 260/306.7 T; 260/465 E; 260/562 R; 548/322; 548/351
[58] Field of Search ............... 260/306.7 T; 424/270

[56] References Cited

U.S. PATENT DOCUMENTS

| | | |
|---|---|---|
| 3,274,209 | 9/1966 | Raeymakers et al. ...... 260/306.7 R |
| 3,364,112 | 1/1968 | Raeymakers et al. ...... 424/270 |
| 4,059,588 | 11/1977 | Baklien et al. ...... 260/306.7 T |

*Primary Examiner*—Donald G. Daus
*Assistant Examiner*—D. G. Rivers
*Attorney, Agent, or Firm*—Lawrence S. Levinson; Merle J. Smith; Burton Rodney

[57] ABSTRACT

Imidazo[2,1-b]thiazole derivatives are provided having the structure

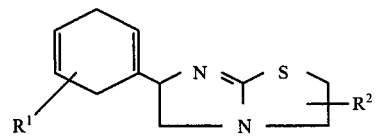

wherein $R^1$ is hydrogen, lower alkyl or carboxy, and $R^2$ is hydrogen, lower alkyl or phenyl.

In addition, a method is provided for treating or inhibiting helminthiasis by parenterally, perorally or topically administering a pharmaceutical composition containing such imidazo[2,1-b]thiazole derivatives. Pharmaceutical compositions for use in the above method are also provided.

12 Claims, No Drawings

IMIDAZO(2,1-b)THIAZOLE DERIVATIVES, COMPOSITIONS CONTAINING SAME, AND METHOD OF TREATING HELMINTHIASIS

BACKGROUND OF THE INVENTION

U.S. Pat. Nos. 3,274,209 and 3,364,112 to Raeymakers et al, assigned to Janssen Pharmaceutical N.V. disclose 6-substituted-imidazo[2,1-b] thiazole compounds, compositions containing same, and their use as anthelmintic agents. These compounds have the following structure

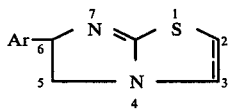

wherein the dotted line between the 2- and 3-positions represents an optional bond, and Ar is a member selected from the group consisting of thienyl, furyl, phenyl and substituted phenyl in which said substituent is a member selected from the group consisting of halo, preferably chloro, bromo and fluoro, nitro, amino and trifluoromethyl; naphthyl, preferably α-naphthyl; and benzyl; provided that, when said Ar is benzyl, a saturated bond exists between the 2- and 3-positions of the imidazo [2,1-b] thiazole nucleus.

DESCRIPTION OF THE INVENTION

The present invention relates to imidazo[2,1-b]-thiazole derivatives having the structure

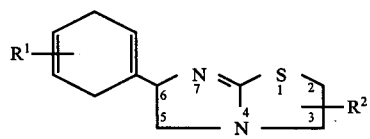

wherein $R^1$ is hydrogen, lower alkyl, or carboxy, and $R^2$ is hydrogen, lower alkyl, or phenyl.

The term "lower alkyl" as used herein includes straight or branched chain aliphatic hydrocarbon radicals having up to and including seven carbon atoms, preferably one to five carbons, such as methyl, ethyl, propyl, isopropyl, n-butyl, isobutyl, t-butyl, amyl, hexyl, heptyl and the like.

Preferred are those compounds wherein $R^1$ is hydrogen, methyl or carboxy, and $R^2$ is hydrogen, methyl (2 or 3), ethyl (2 or 3), or phenyl (2 or 3).

Examples of compounds in accordance with the present invention include the following.

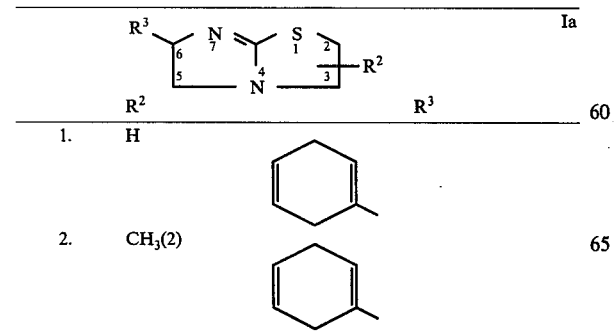

| | $R^2$ | $R^3$ |
|---|---|---|
| 1. | H | [cyclohexenyl] |
| 2. | $CH_3(2)$ | [cyclohexenyl] |
| 3. | $CH_3(3)$ | [cyclohexenyl] |
| 4. | H | [cyclohexenyl-$CO_2H$] |
| 5. | $C_6H_5(2)$ | [cyclohexenyl] |
| 6. | $C_2H_5(3)$ | [cyclohexenyl-$CH_3$] |
| 7. | $CH_3(2)$ | [$CH_3$-cyclohexenyl] |
| 8. | H | [cyclohexenyl-$CO_2H$] |

The compounds of the invention may be prepared in accordance with the following reaction sequence.

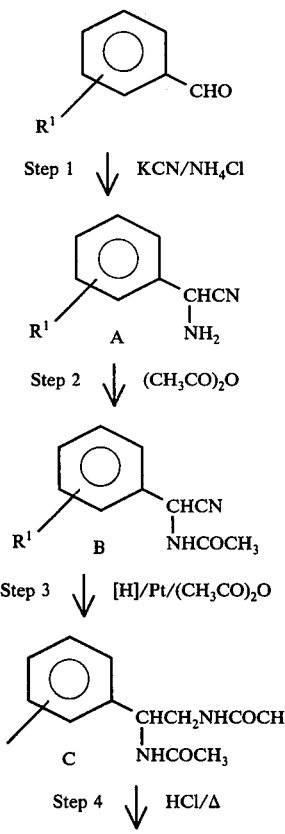

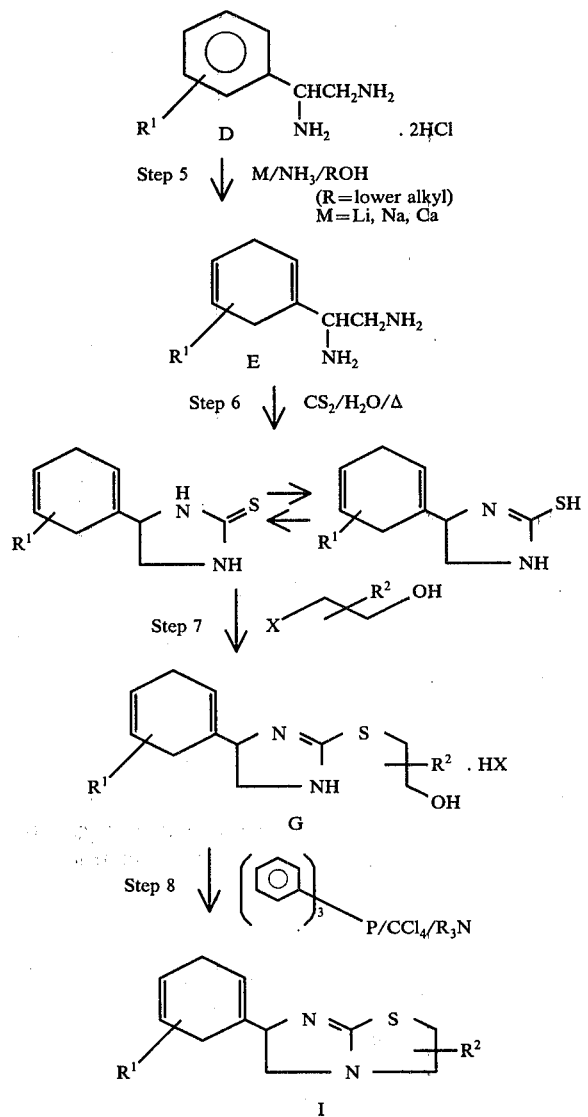

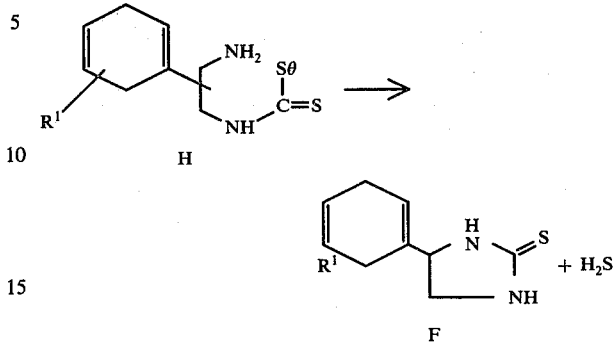

first step is completed in a few minutes, the second step requires reaction times up to 60 minutes.

Alkylation of the thione F to yield the alcohols G (Step 7) is a standard reaction, which can be performed either in the presence or absence of a solvent at temperatures ranging from about 50°–150° for about 30 minutes to 10 hours. Preferred solvents for this operation are alcohols, ethers, glyme, acetonitrile.

The last step in this sequence (Step 8), cyclization of alcohols G to furnish the final products of structure I, is patterned after the method of Appel [Chem. Ber. 108, 2680 (1975) and references therein].

In certain instances, the compounds of formula I form physiologically acceptable acid-addition salts with inorganic and organic acids. These salts frequently provide useful means for isolating the products from reaction mixtures by forming the salt in a medium in which it is insoluble. The free base may then be obtained by neutralization. Then any other salt may again be formed from the free base and the appropriate inorganic acid. Illustrative are the hydrohalides, especially the hydrochloride and hydrobromide which are preferred, sulfate, nitrate, tartrate, methanesulfonate, benzenesulfonate, toluenesulfonate, and the like.

In accordance with the present invention, the compounds of formula I may be administered parenterally, such as subcutaneously, intravenously, intramuscularly or interperitoneally, perorally, or topically (cutaneously), preferably directly onto exposed skin surface, to a mammalian host in the treatment and/or prevention of helminthiasis. Helminthiasis is a parasitic disease which causes widespread and often serious infection in domesticated animals, such as swine, horses, cattle, dogs, cats and sheep. The compounds administered parenterally, perorally, or topically are useful in treating infections caused by Haemonchus, Ostertagia, Trichostrongylus, Cooperia, Dictyocaulus, Nematodirus, Bunostomum, Strongyloides, Oesophagostomum, Trichuris, and liver flukes.

In preparing injectable compositions, the compounds are mixed with a non-toxic, physiologically acceptable non-pyrogenic carrier such as sterile water, sterile saline solution, benzyl benzoate, 1,3-butylene glycol, ethyl oleate, castor oil, glyceryl triacetate, sesame oil, and sesame oil: benzyl benzoate (1:1). The parenteral product will usually take the form of a suspension containing from about 1 to about 10% by weight of the compound of formula I.

The above injectable compositions may also include a non-toxic physiologically acceptable non-pyrogenic suspending agent. Thus, where a non-oily carrier is employed such as water, suspending agents such as In Step 1 of the above reaction sequence, an α-amino nitrile A is prepared by the Strecker synthesis as detailed in *The Merck Index*, 9th Edition, Merck & Co., Inc., Rahway, N.J., 1976, ONR-85.

Acetylation of the α-amino nitrile to the nitrile B (Step 2) is accomplished by standard reaction techniques.

The catalytic reduction of the nitrile B (Step 3) to the acylamines (c) and the hydrolysis of the acylamines C to furnish diamines D (Step 4) have been well-documented (see: Houben-Weyl in *Methoden der Organischen Chemie*, Thieme, Stuttgart, 1957, vol. XI, part 1, pp. 545; 926).

The Birch reduction of the aromatic amines D to furnish the cyclohexadienes E (Step 5) uses well established experimental conditions. (See: A. A. Akhrem et al. in *Birch Reduction of Aromatic Compounds*, IFI/Plenum, New York, 1972).

The ringclosure of the diamines E with carbon disulfide to furnish imidazolidinethiones (Step 6) F is performed in two steps: First, the dithiocarbamate H is prepared by adding carbon disulfide to E which in turn is cyclized in refluxing water to furnish F. Whereas the carboxymethyl cellulose, methyl cellulose, polyvinyl pyrrolidone or non-antigenic gelatin may be employed. Where the carrier employed is an oil, aluminum monostearate may be employed as a suspending agent. The suspending agent may be employed in amounts ranging from about 0.05 to about 2%, and preferably from about 0.1 to about 1% by volume of carrier (the above % may be based on the weight of the carrier where the carrier is qs to 100g).

A non-toxic, non-pyrogenic wetting agent may also be included in the injectable compositions in amounts ranging from about 0.005 to about 0.2% and preferably from about 0.01 to about 0.1% by weight of the carrier. Examples of suitable wetting agents include non-ionic surfactants such as polyoxyethylene sorbitan monostearate, polyoxyethylene sorbitan monooleate [e.g., Tweens] and fatty acid monoglycerides or diglycerides. Other surfactants suitable for use herein are disclosed in the published literature, for example, Kirk-Othmer, Encyclopedia of Chemical Technology, Second Edition, Volume 19, page 507 et seq.

When the compounds of formula I are to be perorally administered in unit dosage form, capsules, boluses or drenches containing the desired amount of anthelmintic distributed in a pharmaceutically acceptable vehicle are usually employed. These are prepared by intimately and uniformly mixing the active ingredient with suitable finely divided diluents, suspending agents, fillers, disintegrating agents and/or binders such as starch, lactose, talc, magnesium stearate, vegetable gums and the like and are compounded by techniques generally known in the art.

The compounds of formula I may also be administered as a component of the feed of the animals or suspended in the drinking water. Thus, novel feed and feed supplement compositions may be prepared in which the compounds of this invention are present as an active anthelmintic ingredient. A typical feed supplement comprises the anthelmintic agent intimately dispersed in or admixed with an inert carrier or diluent, i.e., one that is nonreactive with respect to the anthelmintic agent and that may be administered with safety to the animals. The carrier or diluent is preferably one that is or may be an ingredient of an animal ration. This composition may be mixed with the feed to give any useful desired concentration, preferably about 0.1–2%. Lastly, feeds containing the active ingredient may be made directly by mixing said active ingredient in a feed which is inert to said anthelmintic compounds so as to give feeds having concentrations of anthelmintic agent of from 0.1–2%.

In preparing topical or cutaneous compositions, the anthelmintic compounds are mixed with carriers which are effective in penetrating the skin, whereby the compounds are absorbed by the animal through the skin and transmitted systemically within the animal. A wide range of appropriate carriers may be employed to pass the compound through the skin. The composition employed may be a cream. A liquid composition, however, is particularly convenient to use, e.g., facilitating measuring out doses, and facilitating absorbance through the skin. Thus, a solution or suspension of the compound in a liquid carrier is preferred. Solutions are especially good for transmitting the compound through the skin and are therefore most preferred. The liquid carrier preferably comprises one or more liquids selected from hydrocarbons (e.g., aromatic hydrocarbons, such as an aromatic hydrocarbon fraction of boiling point 130°–250° C, e.g., 180°–220° C, xylene, benzene or toluene, or paraffins, such as those of 6–20 carbon atoms), halogenated aliphatic hydrocarbons (e.g., carbon tetrachloride), ketones (e.g., cyclohexanone or 2-butanone), esters (e.g., ethyl acetate, ethyl benzoate or triacetin), ethers (e.g., diisopropyl ether or tetrahydrofuran), alcohols (e.g., alkanols of 2–8 carbon atoms, such as butyl alcohol, amyl alcohol or isopropyl alcohol, or glycols, such as monopropylene glycol), amides (e.g., dimethylformamide), sulphones (e.g., dimethyl sulphone or sulpholane) and sulphoxides (e.g., dimethyl sulphoxide). In many cases a mixture of liquids is desirable. Preferably the liquid carrier comprises one or more liquids selected from hydrocarbons (e.g., aromatic hydrocarbons especially xylene), alcohols (e.g., isopropyl alcohol or amyl alcohol) and sulphoxides (e.g., dimethyl sulphoxide). Water tends to be ineffective as a liquid carrier for passing the compound through the skin of the animal. Accordingly, the carrier in the liquid compositions preferably comprises an organic liquid.

The viscosity of liquid compositions may be increased over what it would otherwise be by including thickeners which increase the viscosity. This may be desirable in order to retard or prevent the composition from running off the animal.

The additives may include, for example, a surface active agent, an animal fat or wax, e.g., lanolin, a mineral oil, e.g., liquid paraffin, a vegetable oil, e.g., peanut oil, olive oil, corn oil or castor oil, or a polymer, e.g., a hydrocarbon polymer such as polyisobutene.

The surface active agents may comprise anionic compounds for example, soaps, fatty sulphate esters, such as dodecyl sodium sulphate, fatty aromatic sulphonates such as alkylbenzene sulphonates or butyl-naphthalene sulphonates, more complex fatty sulphonates such as the amide condensation product of oleic acid and N-methyl taurine or the sodium sulphonate of dioctyl succinate.

The surface active agents may also comprise nonionic surface active agents such as for example condensation products of fatty acids, fatty alcohols or fatty polyhydric alcohols, or the products obtained from the latter by condensation with ethylene oxide, or the products known as block copolymers of ethylene oxide and propylene oxide. The surface active agents may also comprise cationic agents such as, for example, cetyl trimethylammonium bromide.

The term "surface active agent" is used in the broad sense to cover materials variously called wetting agents, emulsifying agents and dispersing agents.

The composition may contain substances whose taste deters other animals from licking the composition off the animal treated. An example of such a substance is bitter aloes.

Generally, additives facilitating the use in pour-on formulations of other materials, e.g., systemic insecticides, active on animal physiology may be of use also in the present composition.

In general, in carrying out the method of the invention, the parenteral, oral or topical composition described above will be administered to animals in a single dose to provide from about 1 to about 100 mg active compound per kilogram of animal body weight. It is preferred to employ in the range of 2.5–25 mg per kilogram of body weight. The compounds may be divided into a plurality of smaller doses given over one or more days, for example, up to 14 days.

The following examples are provided for illustrative purposes and may include particular features of the invention, however the examples should not be construed as limiting the invention, many variations of which are possible without departing from the spirit or scope thereof. All temperatures are in degrees centigrade.

EXAMPLE 1

6-(1,4-Cyclohexadien-1-yl)-2,3,5,6-tetrahydroimidazol[2,1-b]thiazole, Hydrochloride (1:1)

A. 1-Phenyl-1-acetylaminoacetonitrile

A solution of 240 g KCN, 200 g NH$_4$Cl, 1200 ml of water, 400 g benzaldehyde and 640 ml of methanol is stirred at room temperature for 3 hours. The oily product is separated and the aqueous layer is extracted with ether. The ether extracts and the oily product are combined and extracted with 10% aqueous HCl. The combined HCl-extracts are combined and washed with ether. The HCl-extract is cooled in an ice bath and neutralized with concentrated NH$_3$ solution. The resulting free base is extracted with ether. The dried ether extract is partly evaporated to about 100 ml, cooled, and treated with 130 ml of acetic anhydride. The resulting product is filtered off and crystallized from ethyl acetate ether to yield 165 g of the title A compound, m.p. 108°–110°.

B. 1-Phenyl-1-acetylamino-2-acetylaminoethane

To a solution of 50 g of 1-phenyl-1-acetylaminoacetonitrile in 200 ml of warm acetic anhydride there is added 0.3 g PtO$_2$. This mixture is hydrogenated at 60° and 50 psi. Additional catalyst is added at about 150–170 lbs. of uptake in 0.3 g portions (i.e. 1.2 g of additional catalyst). Total reaction time: 10 hours. The catalyst is filtered off and the solvent evaporated. The solid residue is crystallized from ethyl acetate-ether to yield 31 g of the title B compound, m.p. 154°–156°.

C. 1-Phenyl-1,2-diamino ethane, dihydrochloride

A mixture of 20 g of 1-phenyl-1-acetylamino-2-acetylaminoethane and 100 ml of concentrated HCl is refluxed for 15 hours. The product separates on chilling and is filtered off, washed with acetone and then with ether to yield 13.7 g of the title C compound. This material is stored in the refrigerator (on standing at room temperature, this material will lose part of the bound HCl).

D. 4-(1,4-Cyclohexadienyl)-2-imidazolidinethione

To 1 l. of liquid ammonia there is added with stirring 13.7 g of 1-phenyl-1,2-diamino ethane, dihydrochloride. Then 10 g of Li ribbon is added over a period of 15 minutes. Upon completed addition the dark blue solution is stirred for 15 minutes, after which there is added dropwise 150 ml of absolute ethanol over a period of 75 minutes. After the completed addition, the color of the mixture lightens. The ammonia is evaporated using a warm water bath. The residue is cooled and treated with water. The resulting solution is extracted with CHCl$_3$. The dried organic extract (MgSO$_4$) is evaporated to yield an oil which is free of dissolved ammonia. This oil is dissolved in 50 ml of CHCl$_3$, treated with 30 ml of CS$_2$ and refluxed on the steam bath for 20 minutes. Then 200 ml of water is added. The excess CS$_2$ is boiled off and the remaining mixture is refluxed until no more H$_2$S evolves (about 20 minutes). On cooling, the product separates and is filtered off, and washed with ice water to yield 11.3 g of the title D compound, m.p. 165°–167°.

E. 2-[[4-(1,4-Cyclohexadienyl-1-yl) 1,5-dihydro-1H-imidazole-2-yl]thio]ethanol, hydrobromide

A mixture of 1.5 g of the above thione, 2 ml of 2-bromoethanol and 4 ml of methanol is refluxed for 5 hours. The solvent is evaporated and the oily residue is crystallized from methanol-acetone to yield 1.5 g of the title E compound, m.p. 106°–108°.

F. 6-(1,4-Cyclohexadien-1-yl)-2,3,5,6-tetrahydroimidazol-[2,1-b]thiazole, hydrochloride

A mixture of 4.5 g of 2-[[4-(1,4-cyclohexadienyl-1-yl)1,5-dihydro-1H-imidazole-2-yl]thio]ethanol, hydrobromide, 4.5 g triphenylphosphine, 30 ml of CH$_3$CN, 4.5 ml of triethylamine and 1.5 ml CCl$_4$ is stirred at room temperature overnight. The solvent is evaporated. The residue is made basic with 10% NaOH and the product is extracted with CHCl$_3$. The dried extract is evaporated and kept under vacuum for about 30 minutes. The oily residue is flushed with nitrogen an then treated with HCl-ether. The solvent is evaporated and the residue treated with small portions of acetone which turns the gummy residue into a solid which is filtered off to yield 2.5 g of the title compound, m.p. 215°–218°.

EXAMPLE 2

6-(1,4-Cyclohexadien-1-yl)-2-methyl-2,3,5,6-tetrahydroimidazol[2,1-b]thiazole, hydrochloride Following the procedure of Example 1, but substituting for 2-bromoethanol in Part E 2-bromopropanol, the title compound is obtained.

EXAMPLE 3

6-(1,4-Cyclohexadien-1-yl)-3-phenyl-2,3,5,6-tetrahydroimidazol[2,1-b]thiazole, hydrochloride Following the procedure of Example 1, but substituting for 2-bromoethanol in Part E 1-phenyl-2-bromoethanol the title compound is obtained.

EXAMPLE 4

6-(3-Carboxy-1,4-cyclohexadien-1-yl)-2-methyl-2,3,5,6-tetrahydroimidazol[2,1-b]thiazole, hydrochloride Following the procedure of Example 1, but substituting for benzaldehyde in Part A 3-carboxybenzaldehyde, and substituting for 2-bromoethanol in Part E 2-bromopropanol, the title compound is obtained.

EXAMPLE 5

6-(4-Methyl-1,4-cyclohexadien-1-yl)-2,3,5,6-tetrahydroimidazol[2,1-b]thiazole, hydrochloride Following the procedure of Example 1, but substituting for benzaldehyde in Part A p-tolualdehyde, the title compound is obtained.

EXAMPLE 6

6-(1,4-Cyclohexadien-1-yl)-2,3,5,6-tetrahydroimidazo[2,1-b]thiazole, hydrochloride (1:1)- Parenteral Formulation A solution suitable for subcutaneous administration is prepared by dissolving 150 mg of 6-(1,4-cyclohexadien-1-yl)-2,3,5,6-tetrahydro-imidazo[2,1-b]thiazole, hydrochloride (1:1) (prepared as described in Example 1) in about 10 ml of water for injection, USP. The resulting solution contains 1.5% by weight of the thiazole compound.

EXAMPLE 7

Testing of Parenteral Formulation of 6-(1,4-cyclohexadien-1-yl)-2,3,5,6-tetrahydro-imidazo[2,1-b]thiazole, hydrochloride (1:1)

The following test is carried out to determine the effectiveness of treating sheep infected with gastrointestinal nematodes by subcutaneously administering a single dose of an aqueous suspension of 6-(1,4-cyclohexadien-1-yl)-2,3,5,6-tetrahydro-imidazo[2,1-b]thiazole, hydrochloride (1:1) prepared in Example 1 so as to inject 15 mg of the above thiazole compound per kg of body weight of the test animal.

Egg per gram of feces (EPG) counts are conducted 2-4 days (avg. 3) prior to subcutaneously administering the above thiazole compound in order to determine the degree of parasitism of the test animal. Generally, animals are used which have at least 10,000 eggs per gram of feces although, on occasion, lambs with 8-9,000 eggs per gram can be used. An average pretreatment EPG is calculated for the test animal and medication is given according to individual body weight (15 mg/kg).

EPG's are conducted daily during the week the animal is on test and the final three (3) EPG's are used to calculate an average post-treatment EPG. The percent reduction in the EPG count for a given compound is calculated by taken the average pretreatment EPG and dividing this figure into the average post-treatment EPG and subtracting the quotient from 100.

The 6-(1,4-cyclohexadien-1-yl)-2,3,5,6-tetrahydroimidazo[2,1-b]thiazole, hydrochloride in the form of an aqueous suspension reduces the fecal egg count (EPG) by 100%, when administered subcutaneously at 15 mg/kg.

What is claimed is:

1. A compound of the structure

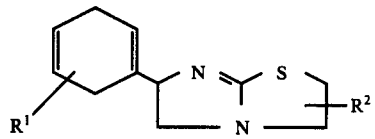

wherein $R^1$ is hydrogen, lower alkyl, or carboxy, and $R^2$ is hydrogen, lower alkyl or phenyl, and physiologically acceptable acid-addition salts thereof.

2. The compound as defined in claim 1 wherein $R^2$ is hydrogen or 2- or 3-lower alkyl.

3. The compound as defined in claim 1 wherein $R^2$ is hydrogen.

4. The compound as defined in claim 1 wherein $R^1$ is hydrogen or 2'- or 3'-lower alkyl.

5. The compound as defined in claim 1 wherein $R^1$ is hydrogen.

6. The compound as defined in claim 1 having the name 6-(1,4-cyclohexadien-1-yl)-2,3,5,6-tetrahydroimidazol-[2,1-b]thiazole, or it hydrochloride salt.

7. A pharmaceutical composition for use in treating or preventing helminthiasis in mammalian species comprising an anthelmintically effective amount of a compound as defined in claim 1 and a non-toxic physiologically acceptable carrier therefor.

8. The composition as defined in claim 7 wherein said compound has the name 6-(1,4-cyclohexadien-1-yl)-2,3,5,6-tetrahydroimidazol-[2,1-b]thiazole, hydrochloride.

9. A method of treating or preventing helminthiasis, which comprises administering to a mammalian host a therapeutically effective amount of a composition as defined in claim 7.

10. The method as defined in claim 9 wherein said composition is administered parenterally.

11. The method as defined in claim 9 wherein said composition is administered perorally.

12. The method as defined in claim 9 wherein said composition is administered topically.

* * * * *